(12) United States Patent
Halvorsen et al.

(10) Patent No.: US 7,771,365 B2
(45) Date of Patent: Aug. 10, 2010

(54) METHOD AND APPARATUS FOR LARYNGEAL EXAMINATION

(76) Inventors: Thomas Halvorsen, Hellebakken 5, 5039 Bergen (NO); Ola Roksund, Marmorneset 1 B, 5232 Paradis (NO); John-Helge Heimdal, Kanonhaugen 36, 5097 Bergen (NO); Britt Skadberg, Geithusvegen 76, 5259 Hjellestad (NO)

(*) Notice: Subject to any disclaimer, the term of this patent is extended or adjusted under 35 U.S.C. 154(b) by 1310 days.

(21) Appl. No.: 11/134,551

(22) Filed: May 20, 2005

(65) Prior Publication Data

US 2006/0069302 A1 Mar. 30, 2006

(30) Foreign Application Priority Data

May 21, 2004 (GB) .................................. 0411440.1

(51) Int. Cl.
*A61B 5/08* (2006.01)
(52) U.S. Cl. ..................... 600/529; 600/101; 600/102; 600/109; 600/160; 600/188
(58) Field of Classification Search ......... 600/529–542, 600/101, 109, 160, 185, 188, 193; 128/201.22–201.26, 128/207.18
See application file for complete search history.

(56) References Cited

U.S. PATENT DOCUMENTS

| | | | | |
|---|---|---|---|---|
| 4,630,614 A | * | 12/1986 | Atlas | .......................... 600/534 |
| 5,431,158 A | * | 7/1995 | Tirotta | ................... 128/206.21 |
| 6,631,713 B1 | * | 10/2003 | Christopher | ........... 128/200.21 |
| 6,790,178 B1 | * | 9/2004 | Mault et al. | .................. 600/300 |
| 2003/0088156 A1 | * | 5/2003 | Berci et al. | .................. 600/188 |

FOREIGN PATENT DOCUMENTS

DE 2454370 A * 6/1975

* cited by examiner

*Primary Examiner*—Robert L Nasser
*Assistant Examiner*—Michael D'Angelo
(74) *Attorney, Agent, or Firm*—Steven M. Jensen; Brian R. Landry; Edwards Angell Palmer & Dodge LLP

(57) ABSTRACT

Method and apparatus for laryngeal examination of a subject (1) during exercise on apparatus such as a treadmill (2), for example to detect laryngeal dysfunction such as vocal cord dysfunction or exercise-induced laryngomalacia. The apparatus comprises a support unit (11) attached to the head (10) of the subject, and a laryngoscope (15) attached to the support unit. The subject exercises whilst the support unit and laryngoscope are attached to the subject. A fibre optic (18) of the laryngoscope is used for transnasal laryngoscopy during exercise and images are stored in a recording device (21).

4 Claims, 2 Drawing Sheets

METHOD AND APPARATUS FOR LARYNGEAL EXAMINATION

CROSS REFERENCE TO RELATED CASE

This application claims priority to and the benefit of United Kingdom Patent Application No. 0411440.1, filed in the United Kingdom on May 21, 2004, the entire contents of which are hereby incorporated by reference.

FIELD OF THE INVENTION

This invention relates to a method and apparatus for laryngeal examination to assist in the diagnosis of breathing difficulties during exercise.

BACKGROUND TO THE INVENTION

Exercise induced asthma (EIA) is characterized by breathing difficulties and wheezing subsequent to exercise. Vocal cord dysfunction (VCD) and exercise-induced laryngomalacia (EIL) are characterised by shortness of breath, stridor, chest pain and occasionally panic reactions during exercise. VCD and EIL may clinically mimic EIA and misdiagnosis should be avoided so that unnecessary asthma medication is not prescribed. However, there have been problems with investigating the situation after a patient has become distressed during exercise, even transnasal laryngoscopy being difficult in such circumstances.

SUMMARY OF THE INVENTION

An object of the present invention is to provide more effective diagnosis of exercise induced breathing distress.

Viewed from one aspect, the invention provides a method of laryngeal examination of a subject to provide image data for use in the diagnosis of breathing distress, comprising the steps of attaching a support unit to the body of the subject, the support unit carrying laryngoscope apparatus, extending a flexible image receiving portion of the laryngoscope apparatus into the larynx of the subject, and subsequently, whilst the subject carries out exercise, monitoring the breathing activity of the subject and recording images from the image receiving portion of the laryngoscope apparatus.

Thus the laryngoscope apparatus for investigation of the larynx of the subject, is set up by, for example, positioning a fibre optic in the larynx, before exercise has started and there is a risk of the subject becoming distressed. By recording the pictures from the laryngoscope once exercise has started, it is possible to investigate the pathology when a subject starts to become distressed.

The support unit could be mounted to the body of the subject in any suitable manner, but in a preferred embodiment of the invention is adapted to be attached to the head of a subject, for example having one or more straps passing around and/or over the head, and/or passing under the chin of a subject. The support unit could be in the form of a cap or the like, or an open frame. To provide sufficient support for the laryngoscope apparatus, at least part of the support unit is preferably rigid. The laryngoscope apparatus may be adjustably attached to the support unit.

The laryngoscope apparatus could be the entire body of a laryngoscope. Alternatively, it could comprise sufficient only of a conventional laryngoscope to enable it to perform the required function. For example, some standard parts may be removable, after the fibre optic has been positioned, to reduce the weight or bulk of the apparatus.

The laryngoscope apparatus is preferably connected to an image recording and/or viewing device. This may be via a fibre optic connection, although a cordless solution might also be possible.

In a preferred arrangement, the laryngoscope projects upwardly above a subject's head, if desired at an angle to the vertical. At its lower end there is provided a fibre optic which is used for transnasal laryngoscopy, and at its upper end is a fibre optic for connection to remote apparatus from viewing and/or recording the images received. Preferably, the arrangement is such that the fibre optic to the remote apparatus is held so that it will not interfere with exercise by the subject, such as running.

Preferably, there is included an ergo-spirometry unit. This is provided with a face mask, which is an integrated part of the unit and in the preferred embodiment is an important and necessary part of the head-set securing the laryngoscope to the head and to the face/nose. The laryngoscope needs proper attachment to the face and particularly to the nose. Even small movements of the laryngoscope within the nasal cavity while running, will cause discomfort and pain. The face mask provides support for the laryngoscope and prevent such movements. The face mask also provides the opportunity to collect all air entering and leaving the subject, thus enabling "within exercise spirometry" (i.e. meassurement of airflow such as exercise flow volume loops) and measurement of all relevant parameters of gas exchange, such as oxygen consumption and $CO_2$ production.

Furthermore, in a preferred embodiment a video camera recording the face and the upper part of the external torso of the test person, is an important part of the set-up. Those studying the exercise-session can thereby relate visual impressions from the external of the patient to the laryngeal pathology.

Preferably, breath sounds are also recorded. Those studying the exercise session can thereby relate sounds from the patient to the laryngeal pathology.

In a preferred system, the final output is a multi media session, consisting of a video recording of the larynx in part of the screen, such as the center, and a video recording of the face and the upper part of the torso located in another part of the screen such as the upper corner, as well as an audio-part consisting of the breath sounds. A physician can thereby exactly relate the occurrence of symptoms (wheezing, discomfort, anxiety or panic reactions) to the onset of visual laryngeal pathology. In addition, the ergo-spirometry data give exact information on the extent to which the subject is exhausted. This enables within-subject follow-up studies in terms of improvements of peak $VO_2$ after intervention, and also for between-subject comparative studies.

Whilst a totally portable system could be used, with a data recorder on the subject or wireless transmission of image data from the laryngoscope, preferably the exercise is carried out in a limited location. Thus, the exercise may be consist of running or walking on a treadmill or stepping machine, for example, with the entire body upright. Alternatively, the lower part of the body could be seated, for example in a rowing or cycling machine. In general, it is preferred that the subject exercises with at least the upper part of the body directed in an upwards direction.

Viewed from another aspect, the invention provides apparatus for use in laryngeal examination of a subject during exercise, comprising a support unit adapted to be attached to the subject, and laryngoscope apparatus attached to the support unit, the arrangement being such that in use a subject can perform exercises with at least the upper part of the body directed in an upwards direction, whilst the support unit, carrying the laryngoscope apparatus, is attached to the subject.

Viewed from another aspect of the invention, there is provided a method of analyzing exercise induced breathing distress of a subject, comprising the steps of attaching a support unit to the body of the subject, the support unit carrying laryngoscope apparatus, extending a flexible image receiving portion of the laryngoscope apparatus into the larynx of the subject, subsequently, whilst the subject carries out exercise and at least when the subject's breathing is distressed, recording data relating to the breathing activity of the subject and recording images from the image receiving portion of the laryngoscope apparatus; and using the recorded breathing activity data and images to distinguish between exercise induced asthma and other causes of breathing distress.

BRIEF DESCRIPTION OF THE DRAWINGS

The invention will be better understood by reading the following description of a preferred embodiment of the invention by way of example only, and with reference to the accompanying drawings, in which.

DESCRIPTION OF PREFERRED EMBODIMENT

Figure 1:
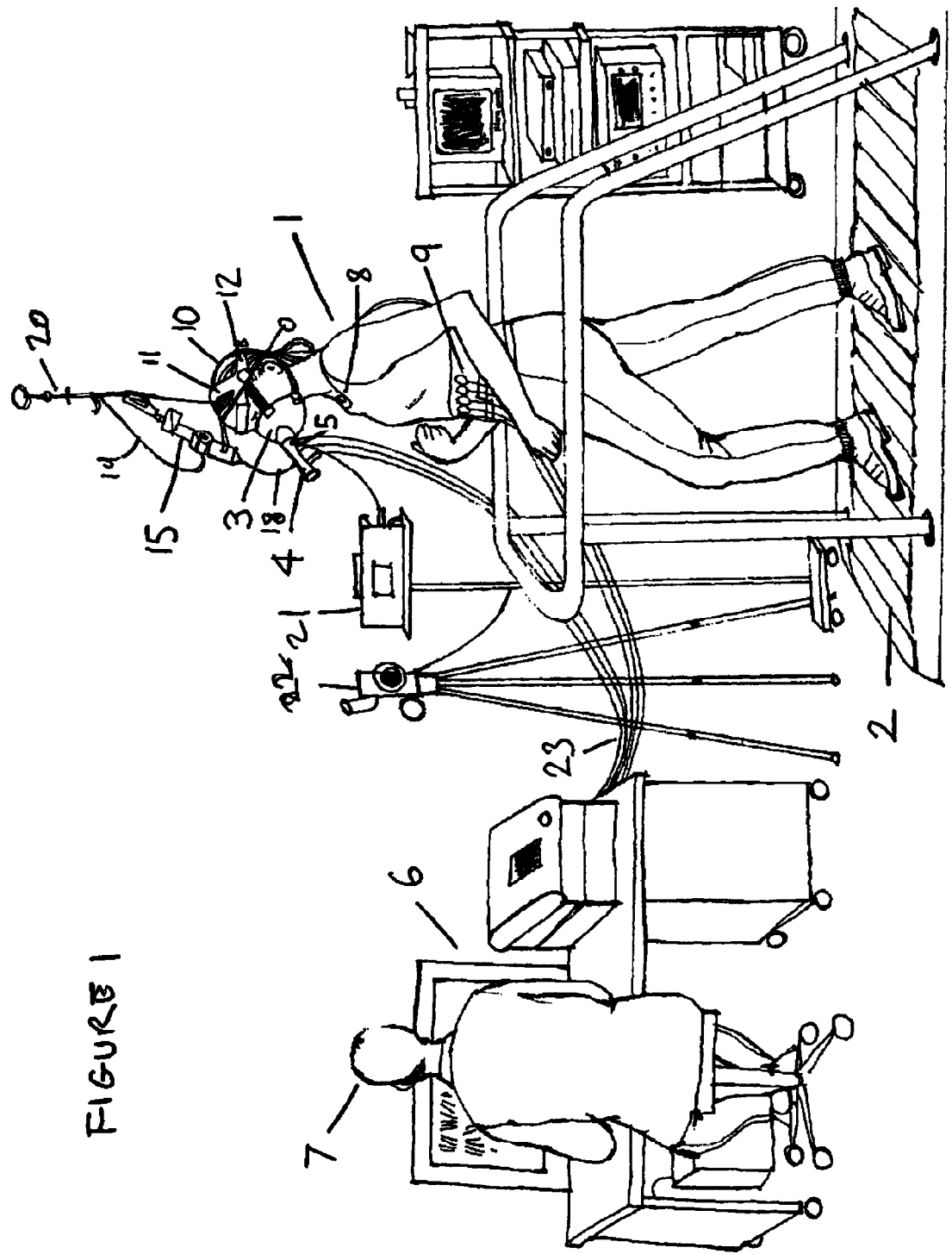
FIG. 1 is an overview of a subject being monitored in accordance with the invention.
Figure 2:
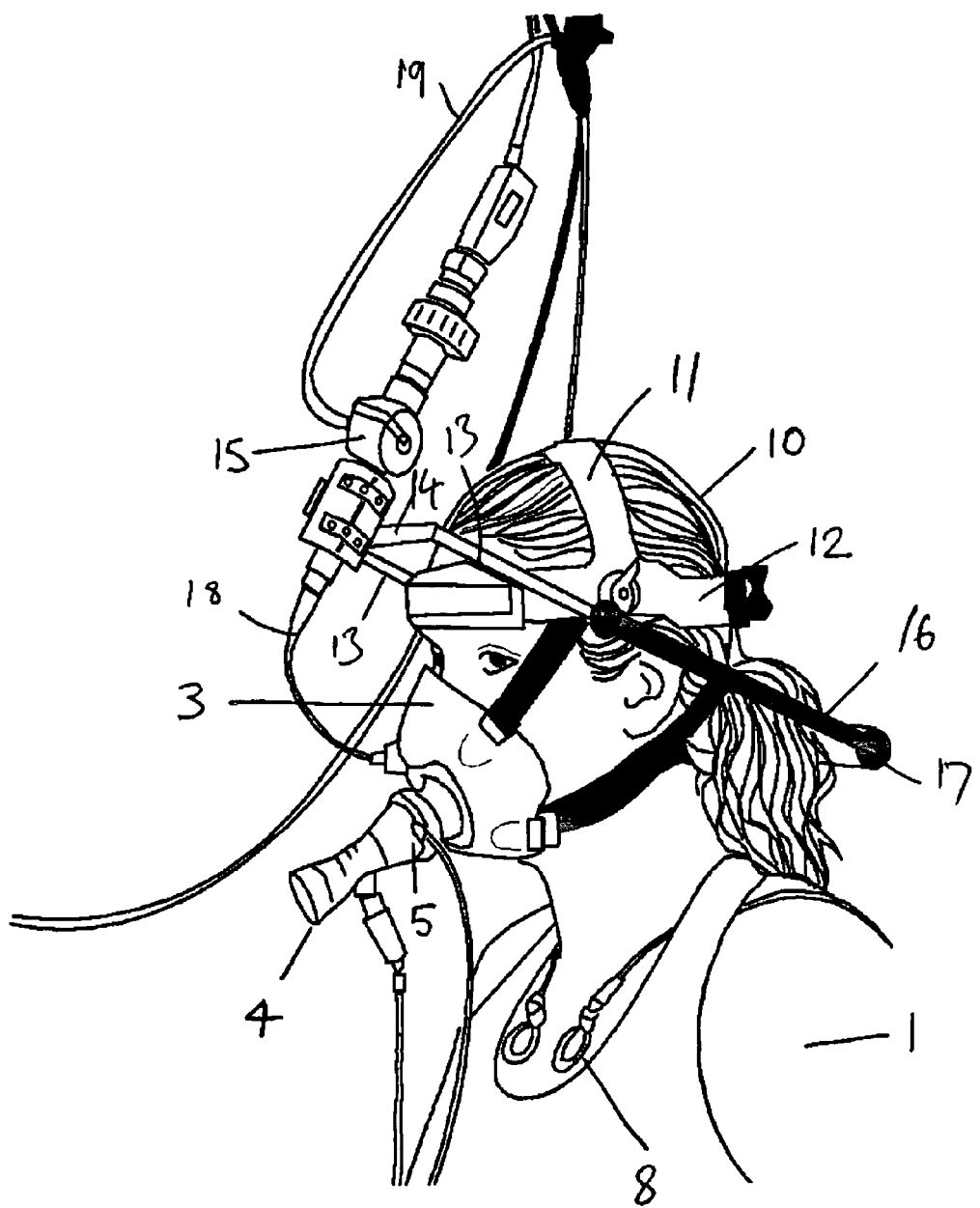
FIG. 2 is an enlarged view showing laryngoscope apparatus on the head of the subject.

Referring now to the drawings, FIG. 1 shows a human subject 1 on a treadmill 2, on which the subject can exercise by running and walking as appropriate. The subject is wearing a mask 3 incorporating a spirometer 4 and other sensors 5 so that during exercise parameters of gas exchange, exercise flow volume loops and breath sounds are continuously recorded and can be observed at a control station 6 by an operator 7. Other sensors elsewhere, such as sensors 8 in the region of the chest and sensors 9 on the abdomen, may detect, for example, pulse rate, blood pressure and respiration.

Attached to the head 10 of the subject is a support unit 11 with straps 12 passing over and around the head, which are secured to provide a firm connection between the user and the unit 11. The support unit carries a pair of pivotally mounted adjustable arms 13, one on each side of the head, interconnected by a member 14 which is spaced from and extends across the forehead of the subject. On the member 14 is mounted the body of a laryngoscope 15 which projects, in the longitudinal direction, upwardly above the head 10 of the subject and towards the rear somewhat. A pair of rearwardly projecting arms 16, one either side of the head 10, are interconnected by a counterbalance 17, padded for comfort and safety, which serves to counteract the weight of the laryngoscope. These are extensions of arms 13, and pivot with them.

A fiber optic 18 extends from the laryngoscope and passes through the mask 3 and transnasally into the larynx of the subject. This is used to observe the larynx of the subject whilst exercising. A fibre optic 19 extends from the body of the laryngoscope, to the end of a support 20 above the subject's head, and then to a recording device 21 which stores the images from the laryngoscope.

A video camera 22 is provided to record the image of the subject during exercise.

Data from the recording device, the video camera, the spirometer and other sensors 5, 8 and 9 is supplied by cables 23 to the control station 6, for data to be processed and presented to the operator 7

Thus, whilst the subject is exercising, images from the laryngoscope can be recorded. When other systems detect distress, for example difficulty breathing, the image from the laryngoscope at that time cam be studied to look for pathological signs.

In tests using the above system, twelve non-symptomatic controls and 40 children (in these tests down to 8 years old) and adolescents with a history of breathing difficulties during exercise were studied with transnasal laryngoscopy while they were running to exhaustion on a treadmill. A classification system for visualized abnormal laryngeal response to exercise was developed, ranging from normal (grade 1) to definite adduction of enlarged aryepiglottic folds and vocal cords (grade 4). Ten control subjects had normal laryngeal responses to exercise, while two had mild abnormalities (grade 2). Ten symptomatic subjects were normal, eighteen were classified as grade 2, four as grade 3 and nine as grade 4. Visual laryngeal pathology always preceded development of anxiety or panic reactions.

Surgical intervention was conducted in four subjects from the most severe group, all with good clinical results, improved parameters of gas exchange and enhanced maximum oxygen consumption.

Using the apparatus and methods of the invention, it was found that exercise induced laryngeal dysfunction (EILD) is not uncommon. The laryngeal response during exercise could be continuously visualized to appreciate the development of pathology and to avoid confusion with psychogenic conditions. If exercise related stridor is clinically suspected, transnasal flexible laryngoscopy during exercise can be performed using the apparatus and methods of the invention.

Before a test, the subject receives decongestant nasal drops and local anesthetics (such as lidocain spray in the nasal cavity). These are extremely commonly used drugs with virtually no side effects.

Most teenagers and children struggling with respiratory problems in relation to exercise are highly motivated to sort out the problems, as they have experienced no effect of the often prescribed asthma treatment they have received. The present invention provides a significant step towards achieving this.

What is claimed is:

1. A method of analyzing exercise induced breathing distress of a subject, comprising the steps of attaching a support unit to the body of the subject, the support unit carrying laryngoscope apparatus, extending a flexible image receiving portion of the laryngoscope apparatus into the larynx of the subject, subsequently, whilst the subject carries out exercise and at least when the subject's breathing is distressed, recording images from the image receiving portion of the laryngoscope apparatus; and using the images to diagnose the cause of breathing distress, wherein data relating to breathing activity of the subject is recorded simultaneously with the images, and the recorded breathing activity data and images are processed and presented by a control station and used to distinguish between breathing distress caused by exercise induced asthma and laryngeal dysfunction, including at least one of vocal cord dysfunction and exercise-induced laryngomalacia.

2. A method as claimed in claim 1, wherein the step of simultaneously recording data relating to breathing activity is carried out using a spirometer.

3. A method as claimed in claim 2, including the step of simultaneously recording breathing sounds of the subject.

4. A method as claimed in claim 1, wherein the subject performs exercises with at least the upper part of the body directed in an upwards direction.

* * * * *